US007666685B2

(12) United States Patent
Bazemore et al.

(10) Patent No.: US 7,666,685 B2
(45) Date of Patent: Feb. 23, 2010

(54) SCREENING METHOD FOR IDENTIFICATION OF COMPOUNDS SUITABLE FOR TREATMENT OF ORAL CAVITY MALODOR ASSOCIATED WITH CONSUMPTION OF GARLIC

(75) Inventors: Russell A. Bazemore, Naperville, IL (US); Charles J. Harrison, Chicago, IL (US); Michael J. Greenberg, Northbrook, IL (US)

(73) Assignee: Wm. Wrigley Jr. Company, Chicago, IL (US)

( * ) Notice: Subject to any disclaimer, the term of this patent is extended or adjusted under 35 U.S.C. 154(b) by 738 days.

(21) Appl. No.: 11/461,848

(22) Filed: Aug. 2, 2006

(65) Prior Publication Data

US 2007/0031350 A1    Feb. 8, 2007

Related U.S. Application Data

(60) Provisional application No. 60/704,597, filed on Aug. 2, 2005, provisional application No. 60/752,678, filed on Dec. 21, 2005.

(51) Int. Cl.
*G01N 33/02* (2006.01)
(52) U.S. Cl. ............... 436/120; 436/121; 436/175; 436/181; 422/5; 422/84; 422/89
(58) Field of Classification Search ........... 436/120, 436/121, 175, 181; 422/5, 84, 89
See application file for complete search history.

(56) References Cited

U.S. PATENT DOCUMENTS

| | | | |
|---|---|---|---|
| 4,112,066 | A | 9/1978 | Hussein |
| 4,131,687 | A | 12/1978 | Mussinan et al. |
| 4,775,537 | A | 10/1988 | Calabro et al. |
| 5,286,501 | A | 2/1994 | Song et al. |
| 6,030,605 | A | 2/2000 | D'Ameila et al. |
| 6,479,082 | B1 | 11/2002 | Johnson et al. |
| 6,537,595 | B1 | 3/2003 | Hyodo et al. |
| 6,627,234 | B1 | 9/2003 | Johnson et al. |
| 6,899,901 | B2 | 5/2005 | Nakatsu et al. |
| 2003/0100842 | A1 | 5/2003 | Rosenberg et al. |
| 2005/0207993 | A1 | 9/2005 | Bazemore et al. |
| 2006/0275222 | A1 | 12/2006 | Dodds et al. |
| 2008/0008665 | A1* | 1/2008 | Ramji et al. ............ 424/48 |

FOREIGN PATENT DOCUMENTS

| | | |
|---|---|---|
| EP | 0265386 A2 | 4/1988 |
| EP | 1020177 A1 | 7/2000 |
| EP | 1195099 A2 | 4/2002 |
| WO | 0023040 A1 | 4/2000 |
| WO | 03105794 A1 | 12/2003 |
| WO | 2004073669 A1 | 9/2004 |
| WO | 2005048965 A2 | 6/2005 |

OTHER PUBLICATIONS

Suarez, F. et al., "Differentiation of Mouth Versus Gut as Site of Origin of Odoriferous Breath Gases After Garlic Ingestion", The American Journal of Physiology, (1999), pp. G425-G430, vol. 276:2:1.
International Search Report dated Dec. 6, 2006 from PCT/US2006/030163.
Dwivedi et al., "Essential oil composition of different accessions of Mentha x piperita L. grown on the northern plains of India", Flavour and Fragrance Journal, 19(5), pp. 437-440, 2004.
Bazemore, R. et al., "Identification of Components Responsible for the Odor of Cigar Smoker's Breath", Journal of Agricultural and Food Chemistry, (2006), pp. 497-501, vol. 54:2.
Acree, T.E. et al., "A Procedure for the Sensory Analysis of Gas Chromatographic Effluents", Food Chemistry, (1984), pp. 273-286, vol. 14.
Block, E., "The Chemistry of Garlic and Onions", Scientific American, (1985), pp. 114-119, vol. 252:3.
Cadwallader, K.R. et al, "Characterization of Saffron Flavor by Aroma Extract Dilution Analysis", American Chemical Society, (1997), Chapter 7, pp. 66-79.
Calvey, E.M. et al., "Supercritical Fluid Chromatography of Garlic (Allium sativum) Extracts with Mass Spectrometric Identification of Allicin", Journal of Chromatographic Science, (1994), pp. 93-96, vol. 32.
Higuchi, O. et al., "Antioxidative Activity of Sulfur-Containing Compounds in Allium Species for Human Low-Density Lipoprotein (LDL) Oxidation in Vitro", Journal of Agricultural and Food Chemistry, (2003), pp. 7208-7214, vol. 51:24.
Lawson, L.D. et al., "Allicin and Allicin-Derived Garlic Compounds Increase Breath Acetone through Allyl Methyl Sulfide: Use in Measuring Allicin Bioavailability", Journal of Agricultural and Food Chemistry, (2005), pp. 1974-1983, vol. 53:6.
Lawson, L.D. et al., "Identification and HPLC Quantitation of the Sulfides and Dialk(en)yl Thiosulfinates in Commercial Garlic Products", Journal of Medicinal Plant Research, (1991), pp. 363-370, vol. 57.
Miranda-Lopez, R. et al., "Odor Analysis of Pinot Noir Wines from Grapes of Different Maturities by a Gas Chromatography-Olfactometry Technique (Osme)", Journal of Food Science, (1992), pp. 985-993 and 1019, vol. 57:4.
Negishi, O. et al., "Effects of Food Materials on Removal of Allium-Specific Volatile Sulfur Compounds", Journal of Agricultural and Food Chemistry, (2002), pp. 3856-3861, vol. 50:13.

(Continued)

*Primary Examiner*—Lyle A Alexander
(74) *Attorney, Agent, or Firm*—Armstrong Teasdale LLP

(57) ABSTRACT

This invention generally relates to a screening method for identifying compositions suitable for use in an oral composition (e.g., a confection or chewing gum product) effective for the treatment of oral cavity malodor associated with the consumption of garlic. In particular, this invention relates to a screening method for determining the ability of a composition to reduce the concentration of a sulfide or disulfide compound (e.g., diallyl disulfide) present in a model sample or solution which is representative of the oral cavity of a subject after consuming garlic, as an indicator of the effectiveness of that composition in the treatment of oral cavity malodor associated with the consumption of garlic.

23 Claims, 11 Drawing Sheets

OTHER PUBLICATIONS

Rosen, R.T. et al., "Determination of Allicin, S-Allylcysteine and Volatile Metabolites of Garlic in Breath, Plasma or Simulated Gastric Fluids", J. Nutri., (2001), pp. 968S-971S, vol. 131.

Rybak, M.E. et al., "Quantitative Determination of Allicin in garlic: Supercritical Fluid Extraction and Standard Addition of Allin", Journal of Agricultural and Food Chemistry, (2004), pp. 682-687, vol. 52:4.

Springett, M.B. et al., "Use of Fiber Interface Direct Mass Spectrometry for the Determination of Volatile Flavor Release from Model Food Systems", Journal of Agricultural and Food Chemistry, (1999), pp. 1125-1131, vol. 47:3.

Tamaki, T. et al., "Volatile Sulfur Compounds in Human Expiration after Eating Raw or Heat-Treated Garlic", Journal of Nutritional Science and Vitaminology, (1999), pp. 213-222, vol. 45:2.

Zhang, Z. et al., "Headspace Solid Phase Microextraction", Anal. Chem., (1993), pp. 1843-1852, vol. 65:14.

Payne, R.K. et al., "Released Oral Malodors Measured by Solid Phase Microextraction-Gas Chromatography Mass Spectrometry", American Chemical Society, (2000), Chapter 7, pp. 73-86.

* cited by examiner

SCREENING METHOD FOR IDENTIFICATION OF COMPOUNDS SUITABLE FOR TREATMENT OF ORAL CAVITY MALODOR ASSOCIATED WITH CONSUMPTION OF GARLIC

REFERENCE TO RELATED APPLICATIONS

This application claims the benefit of U.S. Provisional Application Ser. No. 60/704,597, filed Aug. 2, 2005, and U.S. Provisional Application Ser. No. 60/752,678, filed Dec. 21, 2005, the entire contents of which are incorporated herein by reference.

FIELD OF THE INVENTION

This invention generally relates to a screening method for identifying compositions suitable for use in an oral composition (e.g., a confection or chewing gum product) effective for the treatment of oral cavity malodor associated with the consumption of garlic. In particular, this invention relates to a screening method for determining the ability of a composition to reduce the concentration of a sulfide or disulfide compound (e.g., diallyl disulfide) present in a model sample which is representative of the oral cavity of a subject after consuming garlic, as an indicator of the effectiveness of that composition in the treatment of oral cavity malodor associated with the consumption of garlic.

SUMMARY OF THE INVENTION

Briefly, therefore, the present invention is directed to methods for identifying a composition suitable for use in an oral composition (e.g., a confection or chewing gum product) effective for reducing oral malodor associated with the consumption of garlic. In one embodiment, the method comprises contacting in a vessel a test composition and a model solution comprising a sulfide or disulfide compound, determining the ability of the test composition to reduce the concentration of the sulfide or disulfide compound in a headspace of the vessel, and preparing an oral composition comprising the test composition.

In another embodiment, the method comprises contacting in a vessel a test composition and a model solution comprising allyl methyl sulfide, dimethyl disulfide, methyl allyl disulfide, methyl-t-propenyl disulfide, and diallyl disulfide, and determining the ability of the test composition to reduce the concentration of one or more of the compounds in the model solution in the headspace of the vessel.

In a further embodiment, the method comprises preparing a plurality of test compositions, contacting in individual vessels each of the test compositions and a model solution comprising a sulfide or disulfide compound present in the oral cavity of a subject as a result of the consumption of garlic, determining the ability of each of the test compositions to reduce the concentration of a sulfide or disulfide compound in the headspace of each of the vessels, and identifying one or more test compositions as effective to reduce the concentration of a sulfide or disulfide compound by at least about 50%.

The present invention is also directed to methods for treatment of oral malodor associated with the consumption of garlic. In one such embodiment, the method comprises administering to a subject a composition effective to reduce the concentration of a sulfide or disulfide compound present in the subject's oral cavity as a result of the consumption of garlic by at least about 20%, wherein the concentration of the composition in the saliva of the subject's oral cavity is less than 5 mg of the composition per ml of saliva.

In another embodiment, the method comprises distributing an oral composition containing an ingredient recognized to reduce the concentration of a sulfide or disulfide compound present in a subject's oral cavity as a result of the consumption of garlic, and encouraging a subject to consume or chew the oral composition to ameliorate oral malodor resulting from the consumption of garlic.

DETAILED DESCRIPTION OF THE PREFERRED EMBODIMENTS

Figure 1:
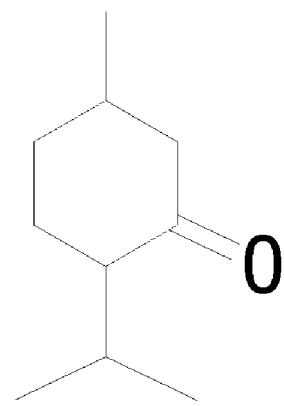
FIG. 1 shows the chemical structure of menthone.

In accordance with the present invention, and as further detailed herein below, it has been discovered that model samples or solutions containing one or more contributors to oral cavity malodor associated with the consumption of garlic (e.g., diallyl disulfide) may be used for evaluating or screening potential active or test compositions (e.g., menthone and caryophyllene) for their ability or effectiveness in reducing the concentration of these contributors to oral cavity malodor in the gaseous atmosphere, or headspace, of a vessel in which they are contained. It has been still further discovered that the ability or effectiveness of an active or test composition to reduce the concentration of one or more of these indicator compounds in the headspace of the vessel is also indicative of the ability or effectiveness of that composition to reduce the concentration of these volatile, odor-causing compounds that are present in a subject's oral cavity due to the consumption of garlic. Accordingly, such an active or test composition may be well-suited for incorporation into an oral composition including, but not limited to, a confection, chewing gum, lozenge, pressed tablet, edible film, mouthspray, mouthwash, or toothpaste product for treatment of oral cavity malodor associated with the consumption of garlic.

Odor-Causing Compounds

Various volatile, sulfur-containing compounds including, for example, various sulfides (e.g., allyl methyl sulfide) and disulfides have been discovered to contribute to oral malodor associated with the consumption of garlic. In particular, it has been discovered that mono- and di-substituted sulfide and disulfide compounds, including for example lower (e.g., C1, C2, C3, C4) alkyl as well as lower alkenyl and/or allyl (e.g., C2, C3, C4) substituted sulfides and/or disulfides, contribute to this oral malodor. These compounds include, for example, allyl methyl sulfide, dimethyl disulfide, methyl allyl disulfide, methyl-t-propenyl disulfide and diallyl disulfide (i.e., allyl disulfide). Garlic and onion are some of the richest sources of dietary sulfhydryl compounds. These compounds are presently believed to be generated from allicin produced as a result of treating (e.g., chopping or crushing) raw garlic and onions. Various other sulfur-containing compounds (e.g., 3,3-thiobis-1-propene) have also been identified as contributors to oral cavity malodor associated with the consumption of garlic.

Techniques for Isolation of Odor-Causing Compounds

In accordance with the present invention, and as noted elsewhere herein, techniques known in the art may be utilized to isolate a sample of a vessel, and in particular the headspace of an airtight or hermetically sealed vessel, containing a model solution which comprises the above-noted compounds that contribute to odor in a subject's oral cavity after consuming garlic. For example, a portion of the headspace of an airtight or hermetically sealed vessel containing such a model solution may be isolated by solid phase microextraction (SPME) and subjected to further analysis (e.g., gas chromatography (GC), used in combination with a device suitable for compound detection or identification, such as a mass spectrometer) to determine the relative proportions of individual compounds contributing to the malodor. In particular, SPME analysis followed by GC analysis may be carried out on a control model or, garlic, solution (i.e., a composition not contacted with a test composition) and a model solution which has been contacted with a test composition, to determine the effect of the test composition on the odorant concentration of the headspace.

Solid phase microextraction is a well-known method suitable for extracting odorous components from a sample for subsequent analysis. In particular, SPME has proven to be suitable for extracting volatile components from the headspace of a vessel in which unconventional odorous substances are contained for subsequent analysis for odor by gas chromatography-olfactometry (GCO) analysis and gas chromatography-mass spectrometry (GC/MS) analysis. (See, for example, *Headspace Solid Phase Microextraction*, Zhang, Z.; Pawliszyn, J.; Anal. Chem. 1993, 65, 1843-1852.) Benefits of SPME include few requirements with respect to sample preparation, little need for solvent, and relatively fast extraction times. Suitable apparatus for the GC/MS analysis include, for example, an Agilent 6890 gas chromatograph (GC)/mass spectrometer (MS) available from Agilent Technologies (Palo Alto, Calif.).

In one approach, a sample known to contain odorants may be analyzed using a gas chromatograph equipped with a mass spectrometer. Identification of the odor-causing components present therein may then generally be performed by matching sample spectra with a database (e.g., Wiley Registry of Mass Spectral Data, 7th Edition, John Wiley & Sons, Inc., 2000) and/or matching retention indices of components of the sample with known standards.

In an alternative approach, identification of the odorants may be conducted by gas chromatography-olfactometry (GCO) analysis, which comprises determining which portions of the GC column eluant exhibit odor associated with the oral cavity of a subject who has consumed garlic utilizing a sniff port, and then subjecting those portions of the eluant to further analysis (e.g., mass spectrometry) to determine their composition. Various GCO techniques have been described in literature. One such method includes the Osme method, described in *Odor analysis of Pinot Noir Wines from Grapes of Different Maturities by a Gas Chromatography-Olfactometry Technique (Osme)*, Miranda-Lopez, R.; Libbey, L. M.; Watson, B. T.; McDaniel, M. R.; J. Food Sci., 1992, 57: 985-993, 1019. Another method includes CHARM analysis, described in *A procedure for the sensory analysis of gas chromatographic effluents*, Acree, T. E.; Barnard, J.; Cunningham, D. G, Food Chem. 1984, 41, 1698-1703. Still another method includes aroma extraction dilution analysis, described in *Characterization of saffron flavor by aroma extract dilution analysis*, Cadwallader, K. R.; Baek; H. H.; Cai, M, *Spices*; Shahidi, F.; Cadwallader, K. R., Eds.; American Chemical Society: Washington, D.C., 1997, 66-79.

It is to be noted that each literature reference mentioned above, or elsewhere herein, is hereby incorporated by reference for all relevant purposes.

Model Solutions

In accordance with the present invention, solutions were prepared which contained the above-noted odor-causing compounds in order to model or mimic saliva present in the oral cavity of a subject who has consumed garlic. These model solutions may be used to determine the potential efficacy of potential active compositions (e.g., test compositions) for ameliorating oral malodor attributed to the consumption of garlic; that is, these model solutions may be used to determine the ability of a test composition to reduce the concentration of one or more of the odor causing compounds present in the gaseous atmosphere, or headspace, in a vessel in which the model solution is contained, which in turn is an indicator of the ability of the test composition to achieve a similar result in a subject's oral cavity. In general, a model solution may be prepared by adding garlic (typically macerated garlic) to a liquid (e.g., aqueous) medium or solvent. The liquid medium typically comprises water, and may optionally comprise one or more additional components (e.g., an alcohol, such as ethanol or methanol). In various embodiments, the aqueous medium to which the garlic is added may comprise a combination of an alcohol (e.g., ethanol) and water, at various concentrations or ratios. For example, a suitable aqueous medium typically contains from about 1% to about 20% (by weight) or from about 1% to about 10% (by weight) of an alcohol such as ethanol, and from about 80% to about 99% (by weight) water (e.g., a 5% ethanol/95% water solution (by weight) or a 1% ethanol/99% (by weight) water solution). To simulate conditions in the oral cavity of a subject who has consumed garlic, preferably the model solution comprises raw, macerated garlic dispersed in water. Thus, typically, the model solution comprises allyl methyl sulfide, dimethyl disulfide, methyl allyl disulfide, methyl-t-propenyl disulfide, diallyl disulfide, and combinations thereof.

Regardless of the medium or solvent used to prepare the model solution, typically garlic is present in the model solution at a concentration of at least about 1% by weight, more typically at least about 5% by weight and, still more typically, at a concentration of at least about 8% by weight. Preferably, garlic is present in the model solution at a concentration of from about 1% to about 20% by weight, more preferably at a concentration of from about 5% to about 15% by weight and, still more preferably, at a concentration of from about 8% to about 12% by weight. Prior to dispersion in the liquid medium, the garlic is typically treated (e.g., chopped, cut or sliced) to ensure release of odor-causing compounds into the solution. Additionally or alternatively, the garlic solution may be agitated (e.g., by blending using suitable apparatus including, for example, a commercial blender available from Waring Commercial (Torrington, Conn.)) to breach intracellular components of the raw garlic and release odor-causing compounds into the solution.

In this regard it is to be noted that, rather than using garlic, in alternative embodiments the odor-causing compounds (e.g., dimethyl disulfide) themselves may be used directly. Regardless of the way in which the model solution is prepared, in general, the model solution is prepared to assure, in the vessel in which it is contained, an initial and final odorant headspace concentration which exceeds the analysis method detection limit sufficiently such that errors in detection/measurement are minimized or avoided.

Screening Method

In accordance with the present invention, the above-noted model solution may be utilized as part of a method for screening a composition to determine whether that composition is effective for reducing odorant concentration in the gaseous atmosphere or headspace of an airtight or hermetically sealed vessel in which a model solution is contained. The vessel in which the model solution is contained is generally of a size appropriate to provide the desired minimum odorant headspace concentration described elsewhere herein. In general, the screening method of the present invention comprises contacting the model solution and a test composition. Generally, the test composition may be in the form of an oil (e.g., menthone or caryophyllene, which may be derived from peppermint oil), in the form of a solution of the test composition in an aqueous medium (e.g., water) or in the form of a solid which is dissolved upon contact with the model solution. The ability of the test composition to reduce the concentration of a sulfide or disulfide compound in the headspace of the vessel in which the model solution is contained may be determined using techniques known in the art. More specifically, this determination may be made by, for example, measuring the concentration of one or more sulfide or disulfide compounds in the headspace of the vessel containing the solution prior to contact with the test composition, and then measuring the concentration of one or more sulfide or disulfide compounds in the headspace of the vessel containing the solution after contact with the test composition. The difference between the initial and final concentration of the sulfide and/or disulfide compound(s) in the headspace of the vessel thus indicates the effectiveness of the test composition for reducing the odorant headspace concentration.

In this regard it is to be noted that, as further detailed elsewhere herein, there has been observed to be a correlation between a quantitative determination of effectiveness of a test composition for reducing odorant headspace concentration and the qualitative performance of an oral composition (e.g., a confection or chewing gum) containing such a composition for treating oral cavity malodor associated with the consumption of garlic.

Both the initial and final sulfide and/or disulfide compound concentrations in the headspace of the vessel are generally determined using means known in the art including, as detailed elsewhere herein, by taking a sample of the headspace and subjecting the sample portion of the vapors to analysis comprising separation, such as by chromatography, and detection, such as by mass spectrometry. Sampling of the headspace may be conducted by contacting the headspace with a fiber effective for absorbing a portion of the vapors comprising a sulfide or disulfide compound in the headspace, or by contacting the headspace with a gas tight syringe effective for extracting a portion of the vapors comprising a sulfide or disulfide compound in the headspace. Sampling or extracting a portion of the headspace is typically conducted at a temperature of from about 20° C. to about 100° C. or from about 20° C. to about 40° C., and preferably from about 20° C. to about 25° C. and, still more preferably, at a temperature of about 22° C. In addition, the sampling or extracting of the headspace typically proceeds over the course of at least about 5 minutes, at least about 10 minutes, at least about 20 minutes, at least about 30 minutes, or at least about 1 hour. Generally, sampling or extraction proceeds over a period of up to about 2 hours, up to about 3 hours, up to about 4 hours, up to about 6 hours, up to about 8 hours, or up to about 10 hours. In various other embodiments, sampling and extraction may proceed over the course of significantly longer periods of time (e.g., up to about 12 hours, up to about 24 hours, or up to about 48 hours). Multiple samples of the headspace may be taken consecutively and, in fact, multiple samples may be extracted during one or more of the sample times set forth above. Additionally or alternatively, samples may be taken intermittently in accordance with the sample times set forth above, with the interval between samplings not narrowly critical.

In this regard it is to be noted that sample analysis and the determination of the concentration of a given odor causing compound in the vessel headspace, either before or after contact of the model solution with a test composition, may be performed using other techniques or methodologies known in the art without departing from the scope of the present invention.

The model solution and the test composition are typically contacted in an airtight or hermetically sealed vessel. To ensure sufficient contact between the test composition and the model solution, the test composition and the model solution are typically contacted for at least about 5 minutes, at least about 10 minutes, at least about 20 minutes, at least about 30 minutes, or at least about 1 hour prior to determining the final sulfide or disulfide compound concentration. Generally, the test composition and the model solution are contacted for a period of up to about 2 hours, up to about 3 hours, up to about 4 hours, up to about 6 hours, up to about 8 hours, or up to about 10 hours, prior to determining the final sulfide or disulfide compound concentration. In various embodiments, the test composition and the model solution are contacted for significantly longer periods of time (e.g., up to about 12 hours, up to about 24 hours, or up to about 48 hours).

A suitable temperature for contacting the test composition and model solution is selected in order to preferably simulate conditions of the oral cavity of a subject, for example, chewing gum, or consuming a confection, in which the test composition would be used. Thus, typically, the test composition and the model solution are contacted at a temperature of from about 20° C. to about 40° C. or from about 20° C. to about 30° C., preferably from about 20° C. to about 25° C. and, still more preferably, at a temperature of about 22° C.

In this regard it is to be noted that the temperature for contact may, in an alternative embodiment, be greater than 40° C. For example, in some embodiments the temperature may be in the range of greater than about 40° C. to less than about 100° C., or between about 50° C. and about 75° C.

The vessel containing the test composition and model solution may also be agitated, for example to simulate chewing conditions. The degree and manner of agitation are not narrowly critical and may be conducted in accordance with methods known in the art.

Typically, the model solution is contacted with a quantity of the test composition that is representative of the amount of test composition that would ultimately be used in an oral composition such as a chewing gum or confection product. For example, the model solution may in some embodiments of the present invention be contacted with at least about 0.1 milligram (mg) of the test composition per gram (g) of solution, at least about 0.2 mg of the test composition per g of solution, at least about 0.3 mg of the test composition per g of solution, at least about 0.4 mg of the test composition per g of solution, at least about 1 mg of the test composition per g of solution, at least about 2 mg of the test composition per g of solution, or at least about 2.5 mg of the test composition per g of solution. In addition, typically the model solution is contacted with less than about 3 mg of the test composition per g of solution. Preferably, the model solution is contacted with from about 0.1 to about 2 mg of the test composition per g of solution, more preferably from about 0.2 to about 1 mg of the test composition per g of solution and, still more preferably, from about 0.3 to about 0.75 mg of the test composition per g of solution.

It is to be noted that the screening method of the present invention is amenable to testing a plurality of compositions using known combinatorial techniques. In such embodiments, a plurality of test compositions (e.g., a library or an array of, for example, at least about 5, at least about 10, at least about 15, at least about 20, at least about 25, at least about 30, at least about 40, or at least about 50 or more test compositions) may be prepared and contacted with the same, or a different, model solution in, for example, individual hermetically sealed vessels, or alternatively in individual hermetically sealed wells of a common substrate. Preferably, the plurality of test compositions are arranged in a spatially addressable format, such as in wells of a common substrate in a spatially addressable format (e.g., a microtiter plate), to enable the present method to be more easily carried out using commercially available automation (e.g., commercially available auto-sampling devices that may be used in combination with, for example, a commercially available GC/MS device). Advantageously, the ability of each of the plurality of test compositions to reduce the concentration of a sulfide or disulfide compound in each of the vessels may be determined in parallel. For example, in various embodiments oral compositions (e.g., confections or chewing gums) containing 2 or more of the plurality of the test compositions are prepared. In certain of these embodiments and various other embodiments, the active composition or compositions used to prepare an oral composition have been identified as providing the greatest reduction in the concentration of a sulfide or disulfide compound as compared to all other of the plurality of test compositions.

Figure 2:
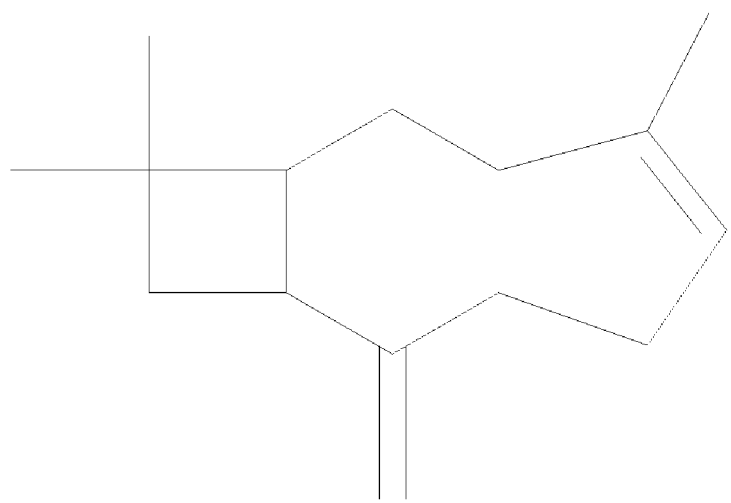
FIG. 2 shows the chemical structure of caryophyllene, and more specifically trans caryophyllene.

Without being bound by a particular theory, reduction of the headspace concentration of a sulfide or disulfide compound attributed to contact with the test compositions as described herein is believed to proceed, at least in part, in accordance with a mechanism which involves an addition reaction between the active and an odor-causing compound. More particularly, an addition reaction is believed to occur between an unsaturated active composition and the sulfide or disulfide compound. For example, the reaction of menthone, which includes a carboxyl group (as shown in FIG. 1), or the reaction of caryophyllene, which is a diene (as shown in FIG. 2), with a sulfide or disulfide compound (e.g., diallyl disulfide), thereby reducing the concentration of the volatile component. For example, the present invention may be utilized to screen test compositions in order to more efficiently identify and select test compositions that are effective to reduce the concentration of a sulfide or disulfide compound in the headspace of a vessel containing a model solution (e.g., as determined by mass spectrometry using means known in the art) by at least about 20% or at least about 30%, preferably at least about 40%, more preferably at least about 50%, still more preferably at least about 60%, still more preferably at least about 70%, still more preferably at least about 80%, still more preferably at least about 90%, and most preferably about 100%.

It is to be noted that the present invention enables the screening of test compositions in a quantifiable, and/or analytical, way, in order to evaluate their potential use in an oral composition, without having to initially prepare an oral composition such as a chewing gum or confection product. As such, a plurality of samples may be evaluated more rapidly and in a more efficient and cost effective manner. For example, in a preferred embodiment, the present invention may be utilized to screen a plurality of test compositions in order to more efficiently identify and select test compositions that are effective to reduce the concentration of one or more sulfide or disulfide compounds in the headspace of a vessel containing a model solution. Once identified, these compositions may then optionally be subjected to further testing, wherein they are formulated into an oral composition for further testing. In particular, one or more of the plurality of test compositions which provide the greatest reduction in the concentration of a disulfide compound in the headspace of the vessel are often formulated into an oral composition. In some instances, these resulting compositions (e.g., gums and/or confections) may achieve the same or similar reduction in the oral cavity of a test subject.

In order for a substance to possess aroma, it typically is volatile and passes through a person's nasal epithelium retronasally (i.e., through the mouth) or orthonasally (i.e., by sniffing). Thus, reduction of the concentration of the volatile odorants in the headspace of a vessel containing a model solution generally indicates effectiveness for reduction of volatile components present in a subject's oral cavity after consumption of garlic and, accordingly, treatment of oral cavity malodor caused by the presence of these volatile components. Accordingly, once a test composition has been successfully identified in accordance with the present invention to reduce the headspace concentration of an odor causing compound, this test composition may then optionally be used to prepare an oral composition (e.g., a chewing gum and/or confection product) using means known in the art, for further evaluation or use with human subjects.

Various compositions may be screened using the process described herein to determine their ability to reduce the odorant concentration in the headspaces of vessels containing model solutions, including compositions derived from various fruits (e.g., cranberries, apples, crabapple, hawthorn berries, plums, prunes and grapes) vegetables and plants. For example, compositions to be screened in accordance with the present invention may comprise, or alternatively consist essentially of, an extract, oil, compound, etc. selected from the group consisting of menthol, menthone, caryophyllene, cranberry extract, Applephenon®, crabapple extract, hawthorn berry extract, plum extract, prune extract, grape seed extract, grape skin extract, cardamom seed extract (e.g., cardamom oil), anethole, alfalfa extract, honeysuckle extract, rosemary extract, basil extract, thyme extract, aloe extract, chrysanthemum extract, green tea extract, coffee berry extract, licorice, parsley seed oil, pine extract, coffee extract, ginseng extract, dandelion root extract, chlorogenic acid, ascorbic acid, caffeic acid, zinc lactate, silica gel, citric acid, maleic acid, tartaric acid, eugenol, α-cyclodextrin, β-cyclodextrin, γ-cyclodextrin, quinic acid and combinations thereof. Carbon (e.g., activated carbon) obtained from, for example, wood or nutshells may also be screened in accordance with the present invention. By way of further example, compositions to be screened in accordance with the present invention typically comprise menthone, caryophyllene, cardamom oil, parsley seed oil, anethole, menthol, and combinations thereof. In accordance with various embodiments, the composition to be screened comprises parsley seed oil, anethole, menthol, and combinations thereof. In still further embodiments, the composition to be screened typically comprises menthone, caryophyllene, cardamom oil, and combinations thereof. In particular, menthone and caryophyllene have been determined to be effective for reducing odorant headspace concentration.

Use of Compositions in Oral Compositions

Compositions recognized as effective to reduce the concentration of a sulfide or disulfide compound in the headspace of the vessel by at least about 50% (or greater) are particularly well-suited for incorporation into an oral composition including, but not limited to, a confection, chewing gum, lozenge, pressed tablet, edible film, mouthspray, mouthwash, foam, or toothpaste product suitable for treatment of oral malodor associated with the consumption of garlic. For example, a test, or an active, composition identified as effective for reducing the concentration of an odor causing compound in the headspace of a vessel, in accordance with the present screening method (e.g., menthone or caryophyllene), is suitable for incorporation into a confection or chewing gum in accordance with methods known in the art as described, for example, in U.S. Pat. No. 6,627,234, the entire contents of which is incorporated herein by reference.

The active composition may be incorporated into an oral composition without dilution, or it may be diluted prior to incorporation. In either case, the active composition may be present in an oral composition (e.g., a confection or chewing gum) at a concentration of at least about 0.05% by weight, more typically at least about 0.08% by weight and, still more typically, about 0.1% by weight. Preferably, the active composition is present in the oral composition at a concentration of from about 0.05% to about 2.5% by weight, more preferably from about 0.08% to about 1.5% by weight and, still more preferably, at a concentration of from about 0.1% to about 1% by weight.

In various preferred embodiments, more than one active composition may be incorporated into a confection or chewing gum. More particularly, those test compositions identified as providing a greater reduction in the concentration of an odor-causing compound in the headspace of a vessel than some or all of the other test compositions may be incorporated into an oral composition. For example, menthone and caryophyllene may be incorporated into a confection or chewing gum product. In such embodiments, menthone and/or caryophyllene is typically present in the confection or chewing gum at a concentration of at least about 0.025% by weight, more typically at least about 0.04% by weight, preferably at a concentration of from about 0.025% to about 0.1% by weight and, still more preferably, at a concentration of from about 0.04% to about 0.06% by weight. As such, these components may be present in the composition at a weight ratio (menthone:caryophyllene, % by weight) of at least about 0.25, typically at least about 0.5 and, more typically, from about 0.75 to about 1.25.

Method of Treating Oral Malodor

Generally, treatment of oral malodor associated with the consumption of garlic proceeds by administration to a subject an oral composition (e.g., one or more pieces of a confection or chewing gum product) containing an active composition identified in accordance with the present invention; that is, oral malodor may be treated in accordance with this invention by administering an oral composition containing a composition recognized to reduce the concentration of garlic odorants in a subject's oral cavity. More particularly, oral malodor may be treated by administering to a subject a composition effective to reduce the concentration of a sulfide or disulfide compound present in the subject's oral cavity as a result of the consumption of garlic by at least about 20%, at least about 30%, at least about 40%, at least about 50%, at least about 60%, at least about 70%, at least about 80%, or at least about 90%. In various such embodiments, the concentration of the composition in the saliva of the subject's oral cavity is less than 5 mg of composition per ml of saliva. It is desirable for the duration of the product in the oral cavity, as well as the rate at which the active composition is released from, for example, a confection or chewing gum, to be controlled so as to optimize the effectiveness of the product in combating oral malodor caused by the consumption of garlic. For example, in the case of a chewing gum, administration typically comprises chewing of the gum for at least about 5 minutes, more typically for about 5 to about 60 minutes, even more typically for about 10 to about 20 minutes and, still more typically, for about 20 minutes. In the case of a chewing gum, typically at least about 5%, at least about 10%, at least about 25%, at least about 50%, at least about 75%, or even about 100% of the active composition is released from the gum during the first few minutes (e.g., the first about 2 minutes, about 3 minutes, about 4 minutes, or even about 5 minutes) of chewing. More typically, at least about 25%, at least about 50%, at least about 75%, or even about 100% of the active composition is released from the gum during the first 20 minutes of chewing.

It is to be noted in this regard, however, that in various alternative embodiments, a more sustained delivery of active composition into the oral cavity may be desired. Thus, in such embodiments it may be desired for no more than about 25%, no more than about 50%, or no more than about 75% of the active composition to release into the oral cavity during the first few minutes (e.g., the first about 2 minutes, about 3 minutes, about 4 minutes, or even about 5 minutes) of administration. Likewise, it may be desired for no more than about 50% or no more than about 75% of the active composition to release into the oral cavity during the first 20 minutes of administration.

Method for Promoting the Use of an Oral Composition

The present invention is also directed to a method for promoting an oral composition (e.g., a chewing gum or confection product) containing a composition effective to reduce the concentration of a sulfide or disulfide compound present in a subject's oral cavity as a result of consuming garlic. Generally, this process comprises distributing, to a subject such as an end user or alternatively to someone who will in turn distribute to an end user, an oral composition including, but not limited to, a confection, chewing gum, lozenge, pressed tablet, edible film, mouthspray, mouthwash, foam, or toothpaste product containing a composition recognized to reduce a concentration of a sulfide or disulfide compound present in a subject's oral cavity as a result of consuming garlic, and encouraging a subject to consume or chew the product to ameliorate oral malodor resulting from consuming garlic. This encouragement may typically appear on a package containing the product and may be disseminated by conventional means (e.g., electronic or print media). Generally, the product is described as containing an ingredient recognized to reduce a concentration of a sulfide or disulfide compound present in a subject's oral cavity as a result of consuming garlic. In particular, the recognition of the ingredient's effectiveness is achieved by carrying out the screening method described herein. In the case of a chewing gum containing such an ingredient, generally the subject is encouraged to chew the gum for a certain period of time (e.g., at least about 5 minutes or about 20 minutes).

The present invention is further illustrated by the following Examples. These Examples are not to be regarded as limiting the scope of the invention or the manner in which it may be practiced.

EXAMPLES

Example 1

The following example details testing of potential active compositions for treatment of solutions with characteristic garlic aroma.

In Vitro Dose Response:

A model solution containing raw chopped garlic (20 g) dispersed in water (200 ml) was prepared by blending in a Waring commercial blender (Waring Commercial, Torrington, Conn.) at low power for 30 seconds and at high power for 30 seconds. The resulting solution was homogeneous with no visible garlic particles present.

A portion of the raw, macerated garlic solution (5 g) was treated with different levels of potential ameliorating actives and the headspace was extracted and analyzed (as described in greater detail below) to determine the effect of the potential actives on the headspace concentration of compounds contributing to oral cavity malodor associated with consumption of garlic. Two actives (menthone and caryophyllene) were tested for such headspace concentration reduction efficacy.

The amounts of actives to be tested were initially determined utilizing bench level sensory screening (i.e., sniffing the odor intensity of a sample of the macerated garlic solution before and after introduction of various amounts of active to determine its effect). Once a level is determined to provide a reduction in odor, greater and lesser amounts are tested in further detail as set forth below.

Menthone was tested at the following levels: 3 mg/g raw garlic solution, 1 mg/g raw garlic solution and 0.3 mg/g raw garlic solution.

Caryophyllene was tested at the following levels: 0.4 mg/g raw garlic solution, 0.24 mg/g raw garlic solution and 0.1 mg/g raw garlic solution.

Headspace of a vessel containing a portion of the garlic solution (5 ml) treated with a potential active was extracted for 60 minutes utilizing solid phase microextraction (SPME) with a 75 µm Carboxen-polydimethyl siloxane fiber (Supelco, Bellefonte, Pa.).

The SPME fiber assembly was injected into an Agilent 6890 gas chromatograph (GC)/mass spectrometer (MS) modified for multidimensional analyses and equipped with a sniff port and Aroma Trax software (Microanalytics, Round Rock, Tex.). Fibers remained in the GC injection port for five minutes following injection.

The GC/MS operating parameters included a He carrier gas flow rate of 6.5 ml/min, split mode (2:1) and the injector set at 250° C. Column 1 was 12 meter, 0.53 mm I.D. with a methyl silica stationary phase. Column 2 was a 25 meter, 0.53 mm DB-5 capillary column. The oven was programmed to hold at 40° C. for 3 minutes and to heat to 220° C. at a rate of 7° C./min and hold at 220° C. for 20 minutes. The MS operated in Electron Impact Mode (E.I.) at 70 eV.

Figure 3:
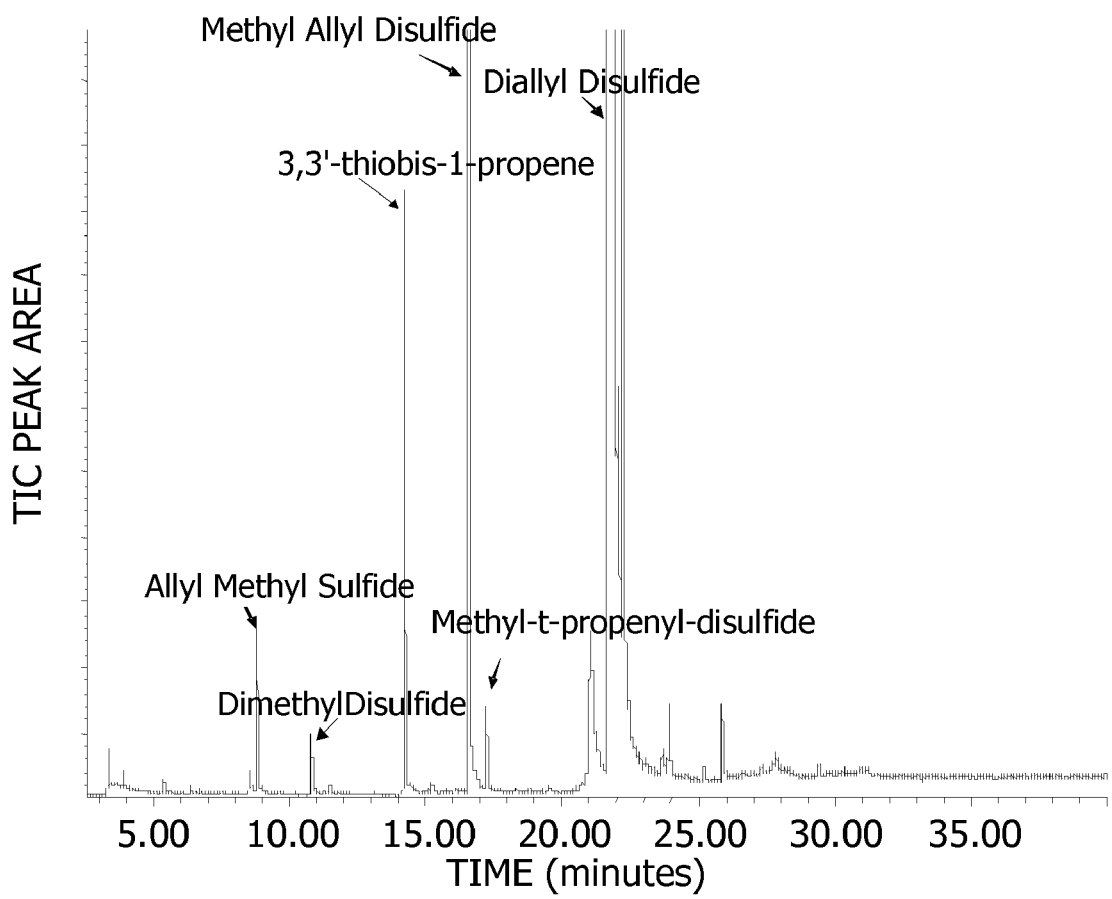
FIG. 3 is a total ion current (TIC) chromatogram prepared as described in Example 1.

The results of GC/MS analysis of the control raw garlic solution are shown in FIG. 3 (a total ion current (TIC) chromatogram of a sample of the headspace of the control solution).

Figure 4:
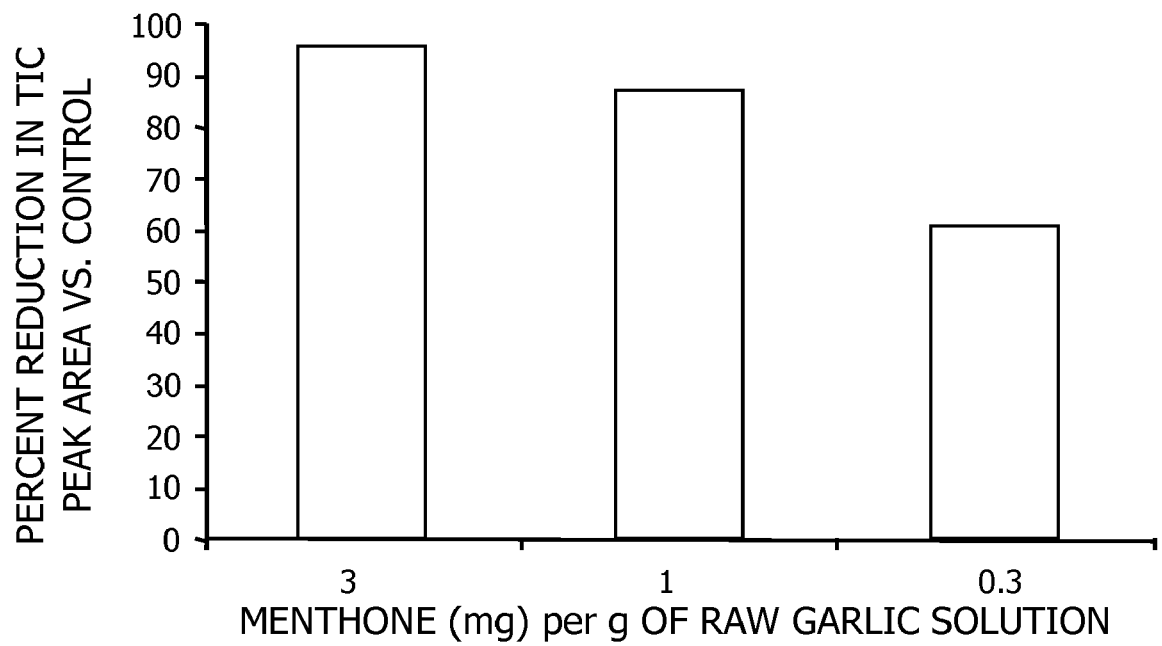
FIG. 4 shows the percent reduction of diallyl disulfide headspace concentration observed with addition of menthone to a raw garlic solution at varying levels as described in Example 1.

Reductions in headspace concentration of diallyl disulfide observed with addition of menthone to a raw garlic solution at varying levels based on comparison with the GC/MS results of the control garlic solution are shown in FIG. 4; Table 1 provides the analytical dose response data. As shown in FIG. 4, menthone reduced the diallyl disulfide headspace concentration of the solution of macerated garlic from 61% (at an active concentration of 0.3 mg/g solution) to 96% (at an active concentration of 3 mg/g solution).

TABLE 1

Menthone (mg menthone per g garlic solution) reduction of diallyl disulfide headspace concentration: analytical dose response data.

| | GC/MS Peak Area | | | |
|---|---|---|---|---|
| | Control | 0.3 mg/g | 1 mg/g | 3 mg/g |
| Run 1 | 154604684 | 58241626 | 16829160 | 4757863 |
| Run 2 | 132204464 | 60764744 | 16827232 | 5868573 |
| Run 3 | 139689604 | 46610414 | 20835556 | 6746448 |
| Mean | 142166251 | 55205595 | 18163983 | 5790961.3 |
| Standard Deviation | 11403631 | 7549793.3 | 2313650.6 | 996561.72 |
| Standard Error | 6583889.4 | 4358875.2 | 1335786.8 | 575365.17 |
| % RSD | 8.02 | 13.67 | 12.73 | 17.20 |

Figure 5:
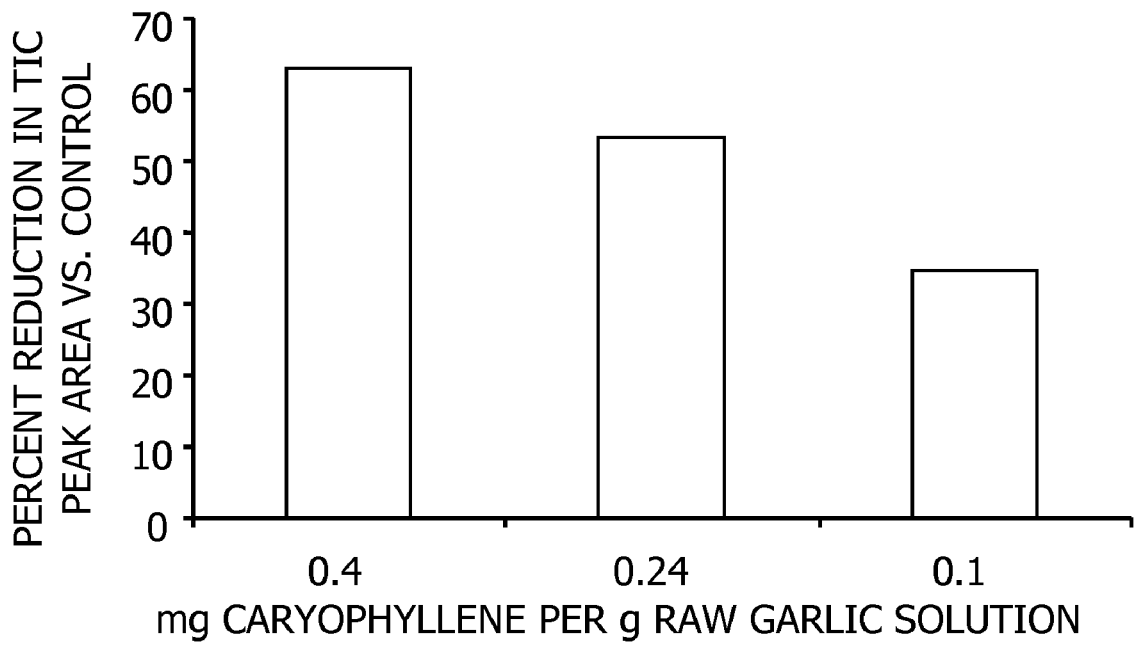
FIG. 5 shows the percent reduction of diallyl disulfide headspace concentration observed with addition of caryophyllene to a raw garlic solution at varying levels as described in Example 1.

Reductions in headspace concentration of diallyl disulfide observed with addition of caryophyllene at varying levels to a raw garlic solution based on comparison with the GC/MS results of the control garlic solution are shown in FIG. 5; Table 2 provides the analytical dose response data. Active levels added were less than used with menthone due to the often-perceived woody flavor of caryophyllene. As shown in FIG. 5, diallyl disulfide headspace levels were decreased from 34% (at an active concentration of 0.1 mg/g) to 63% (at an active concentration of 0.4 mg/g).

TABLE 2

Caryophyllene (mg caryophyllene per g garlic solution) reduction of diallyl disulfide headspace concentration: analytical dose response data.

| | GC/MS Peak Area | | | |
|---|---|---|---|---|
| | Control | 0.4 mg/g | 0.24 mg/g | 0.1 mg/g |
| Run 1 | $1.55 \times 10^8$ | 91167385 | 69400527 | 49803124 |
| Run 2 | $1.32 \times 10^8$ | 94368797 | 61729644 | 56316479 |
| Run 3 | $1.4 \times 10^8$ | 93422075 | 67591321 | 52155883 |
| Mean | $1.42 \times 10^8$ | 92986086 | 66240497 | 52758495 |
| Standard Deviation | 11403631 | 1644635 | 4009882 | 3298227 |
| Standard Error | 6583889 | 949530.5 | 2315107 | 1904233 |
| % RSD | 8.02 | 1.76 | 6.05 | 6.25 |

Comparison of the actives indicates approximate parity between menthone and caryophyllene.

Sensory Analysis:

Sensory analysis of the solutions utilized for analytical analyses of the raw garlic described above was conducted by ten panelists who evaluated the odor intensity of the model solution (raw macerated garlic) with and without the different levels of added active. Odor intensity was assessed utilizing a 0-100 point scale ballot with 0=no odor and 100=very strong odor.

Figure 6:
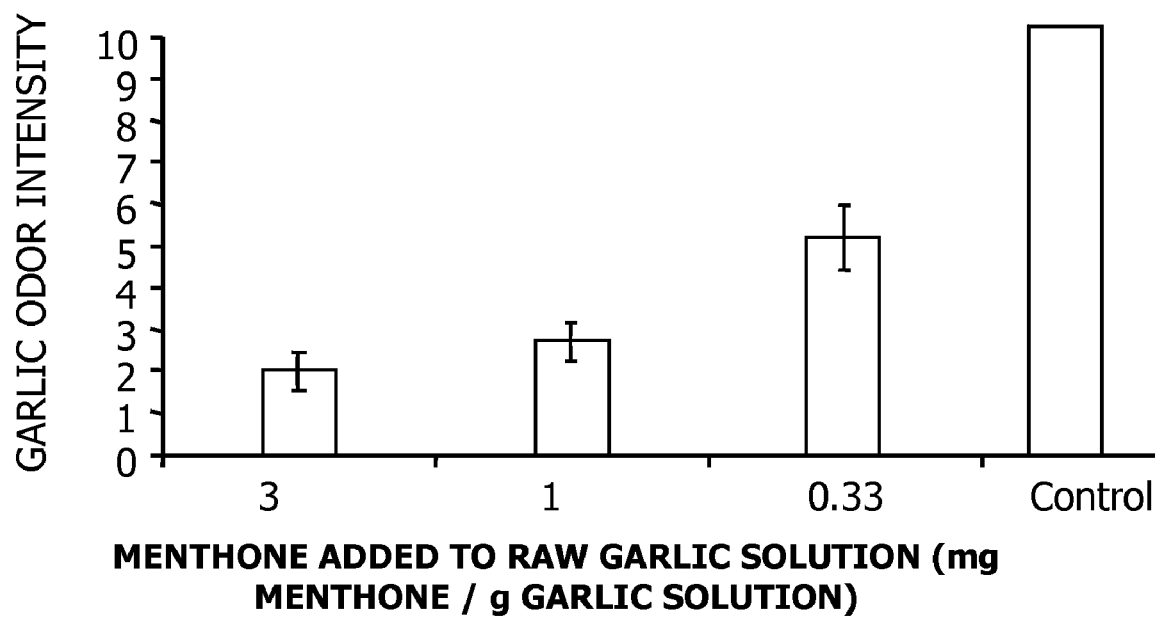
FIG. 6 shows sensory analysis results associated with treatment of a raw garlic solution with varying concentrations of menthone as described in Example 1.

The results for menthone are shown in FIG. 6 and Table 3.

TABLE 3

Panelist responses (N = 10) in rating aroma intensities of garlic odor solution treated with different concentrations of menthone.

| | | Odor Intensity (0–100) | | |
|---|---|---|---|---|
| | Panelist | 3 mg/g | 1 mg/g | 0.33 mg/g |
| 1 | LD | 4 | 2 | 8 |
| 2 | DB | 1 | 2 | 3 |
| 3 | AC | 1 | 4 | 7 |
| 4 | ED | 2 | 1 | 1 |
| 5 | RB | 0 | 2 | 1 |
| 6 | DW | 4 | 2 | 6 |
| 7 | KF | 2 | 4 | 7 |
| 8 | AA | 3 | 6 | 7 |
| 9 | SM | 0 | 2 | 7 |
| 10 | RD | 3 | 2 | 5 |
| | Mean | 2 | 2.7 | 5.2 |
| | Standard Deviation | 1.4 | 1.4 | 2.4 |
| | Standard Error | 0.44 | 0.44 | 0.78 |

Figure 7:
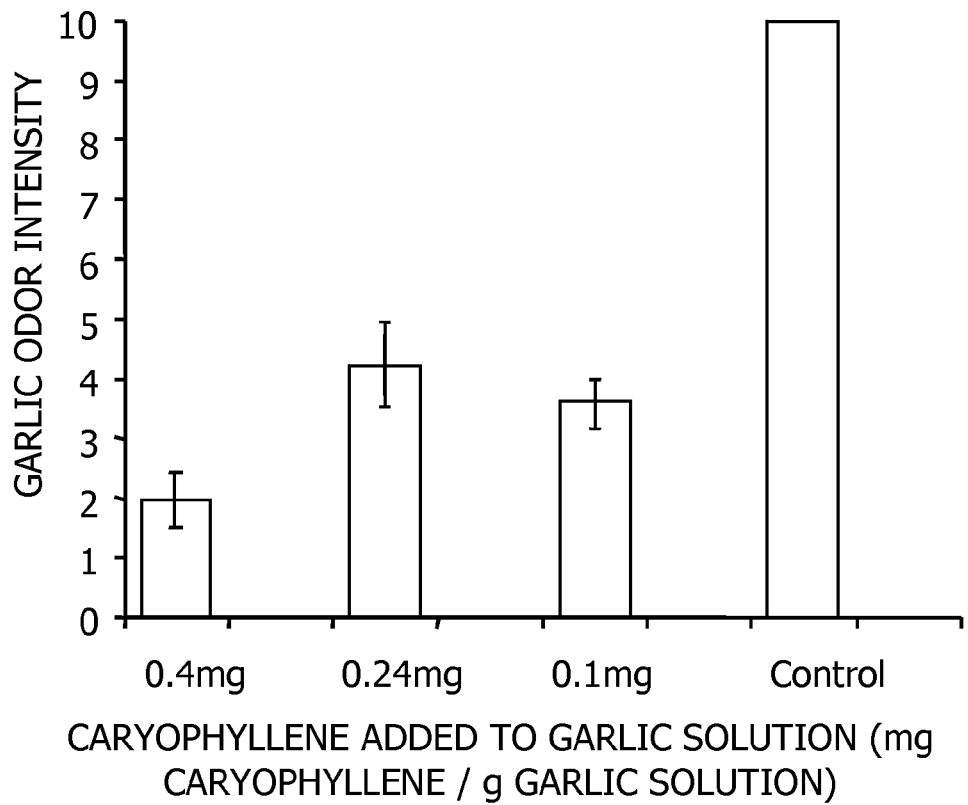
FIG. 7 shows sensory analysis results associated with treatment of a raw garlic solution with varying concentrations of caryophyllene as described in Example 1.

The results for caryophyllene are shown in FIG. 7 and Table 4.

TABLE 4

Panelist responses (N = 10) in rating aroma intensities of garlic odor solution treated with different concentrations of caryophyllene.

| | | Odor Intensity (0–100) | | |
|---|---|---|---|---|
| | Panelist | 0.4 mg/g | 0.2 mg/g | 0.1 mg/g |
| 1 | KF | 3 | 5 | 7 |
| 2 | RB | 1 | 3 | 4 |
| 3 | MT | 2 | 4 | 5 |
| 4 | DB | 5 | 5 | 6 |
| 5 | AC | 3 | 4 | 2 |
| 6 | SM | 4 | 9 | 5 |
| 7 | DC | 4 | 8 | 4 |
| 8 | HV | 3 | 9 | 6 |
| 9 | RB | 4 | 5 | 5 |
| 10 | MH | 0 | 3 | 4 |
| | Mean | 2.9 | 5.5 | 4.8 |
| | Standard Deviation | 1.4 | 2.2 | 1.3 |
| | Standard Error | 0.4 | 0.6 | 0.4 |

The sensory dose response data indicated a trend similar to that exhibited by the analytical, in vitro analysis. As shown in FIG. 6, menthone reduced the odor of raw macerated garlic in water between 48% (at an active concentration of 0.3 mg/g) to 80% (at an active concentration of 3 mg/g). As shown in FIG. 7, caryophyllene addition decreased odor intensities between 52% (at an active concentration of 0.1 mg/g) to 71% (at an active concentration of 0.4 mg/g). Generally, caryophyllene was more effective considering the low concentration of active utilized which provided odor reduction of 71%.

Example 2

This example details active component release (i.e., menthone and caryophyllene) from a standard chewing gum base (utilized in Peppermint Eclipse®, which is commercially available from the Wm. Wrigley Jr. Company (Chicago, Ill.)). Menthone and caryophyllene were added to the gum coating. In order for an active compound to be suitable for use with chewing gum as a delivery vehicle, it typically releases from the gum matrix and into the oral cavity during chewing so that it may interact with garlic odorants present in the oral cavity.

The method to measure active release and rate of release involved having 5 panelists chew one serving of gum each (2 pellets, 1.5 g each), for each of the following times: 5, 10, 20, 25 minutes. After chewing for each time period, gum cuds were collected (a minimum of 6 cuds) and dissolved in a chloroform solvent with undecane as the internal standard. The solution was shaken for six hours to ensure salvation. Liquid was then removed and purified with solid phase extraction (SPE) utilizing a Millipore (Billerica, Mass.) Millex-FH hydrophobic poytetrafluoroethylene (PTFE) membrane having a pore size of 0.45 µm. For non-volatile active components, the aqueous layer was removed and analyzed by high performance liquid chromatography (HPLC).

The amount of active in the extracted liquid phase was used to determine the amount of active released from the gum during chewing. Undecane was utilized as an internal standard and a calibration curve constructed. The chloroform layer (bottom layer) was removed by Pasteur pipette and placed in a GC vial and capped with a crimped cap and Teflon septa. The liquid was injected into the GC (described above in Example 1) for active component quantification utilizing an Agilent 7683 Series Autosampler (Agilent, Palo Alto, Calif.) set to inject 5 µl. Injections are done in triplicate to ensure accuracy and precision.

The active amounts remaining in the gum cuds containing each of the potential actives were compared to a control gum containing the active which was not chewed.

As shown in Table 5, the total amount of menthone in the 2 pellets of control gum (i.e., Peppermint Eclipse®), without additional menthone, was 10.7 mg.

TABLE 5

Menthone in control chewing gum (total in 2 pellets).

| Time (min) | % present in sample | Menthone (mg) |
|---|---|---|
| 0 | 0.357 | 10.7 mg |

When testing menthone as an active, the initial amount was 14.2 mg menthone (i.e., an additional 3.5 mg of menthone).

Figure 8:
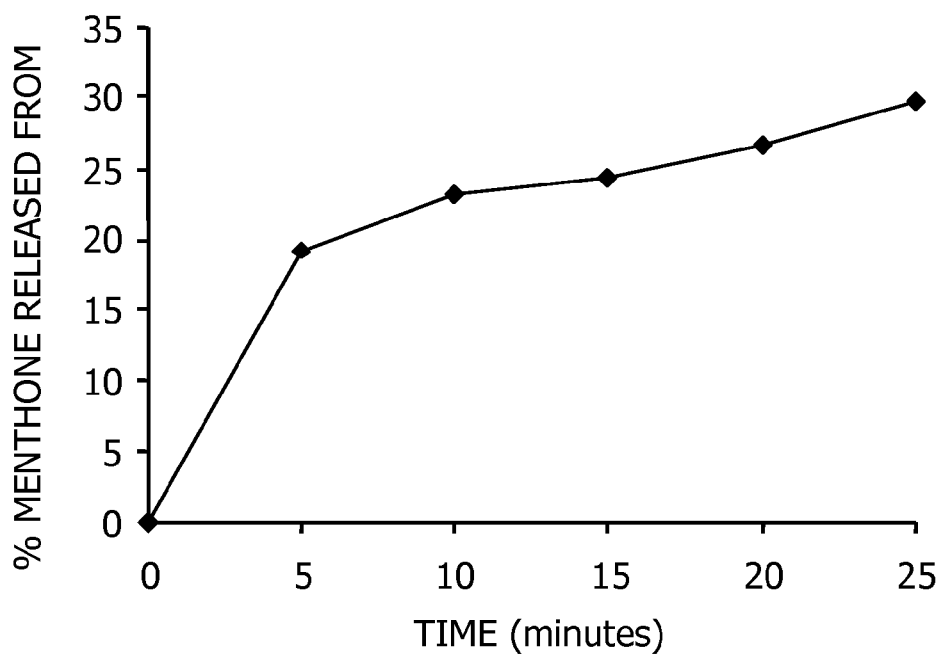
FIG. 8 shows the rate of menthone release during 25 minutes of chewing in terms of the percentage of menthone released from the gum as described in Example 2.
Figure 9:
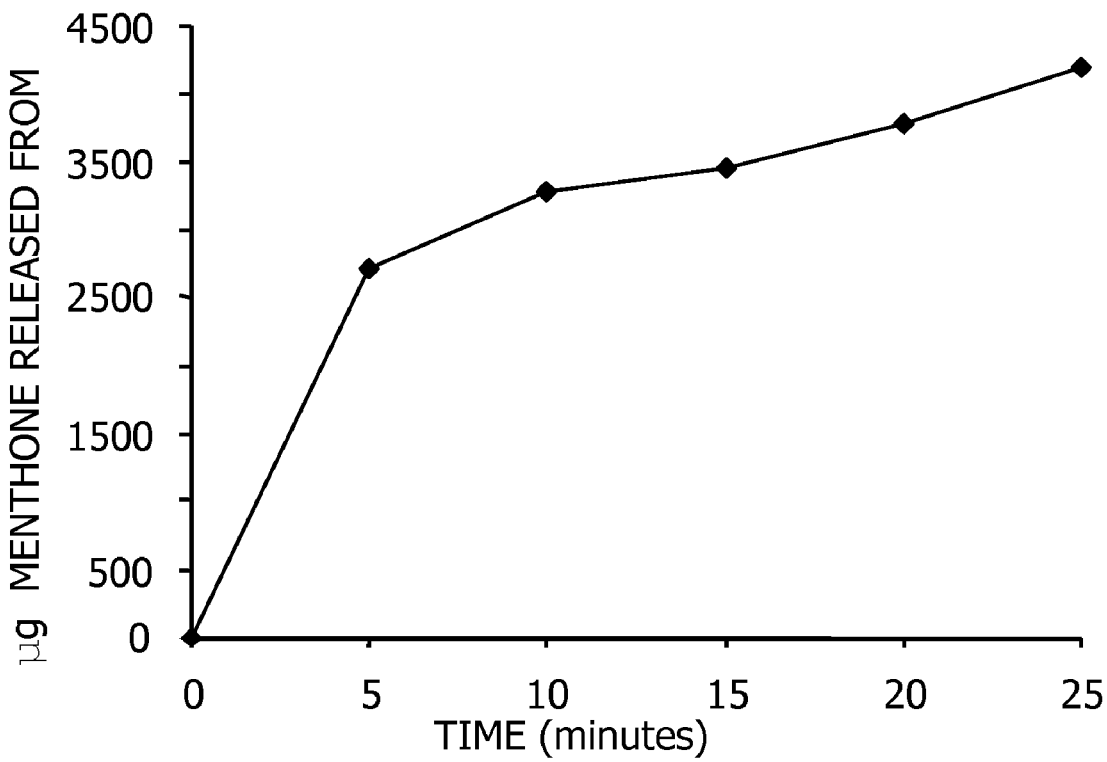
FIG. 9 shows the rate of menthone release during 25 minutes of chewing in terms of the amount of menthone (μg) released from the gum as described in Example 2.

The amount of menthone remaining in the gum after 5, 10, 15, 20 and 25 minutes of chewing was determined. For example, 9.81 mg remained after 25 minutes of chewing. Thus, thirty-one percent (4.39 mg) of menthone were released during 25 minutes of chewing. FIGS. 8 and 9 show the rate of menthone release during 25 minutes of chewing in terms of the percentage of menthone released from the gum and amount (μg) of menthone released from the gum, respectively.

As shown in Table 6, the total amount of caryophyllene in the 2 pellets of the control gum, without additional caryophyllene, was 1.35 mg.

TABLE 6

Caryophyllene in control chewing gum (total in 2 pellets).

| Time (min) | % present in sample | caryophyllene (mg) |
|---|---|---|
| 0 | 0.023 | 1.35 mg |

Figure 10:
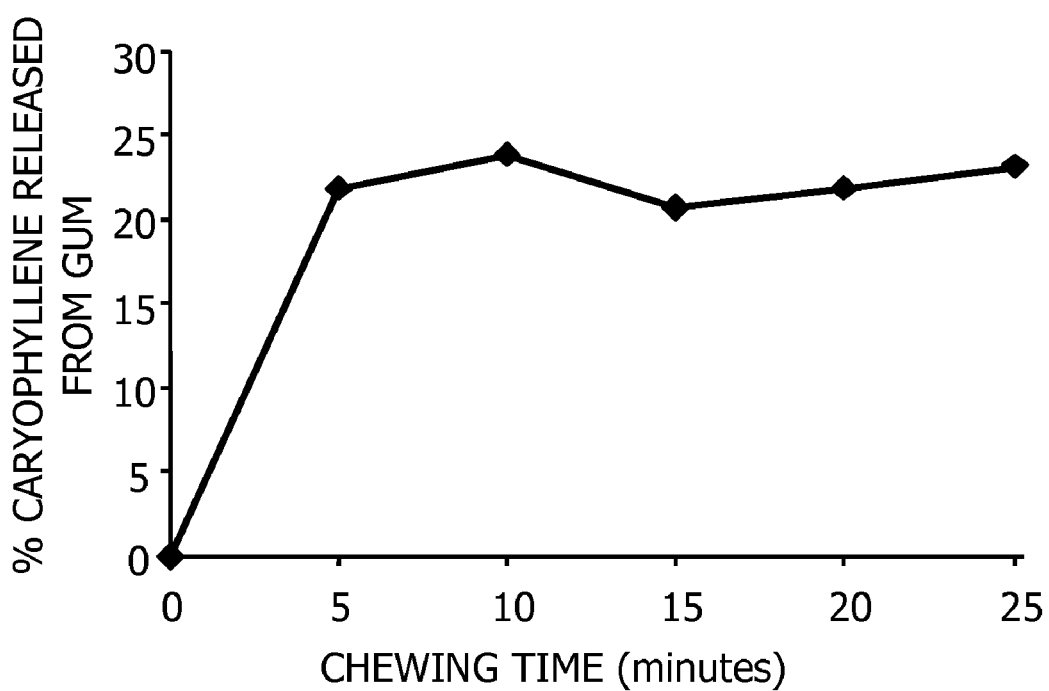
FIG. 10 shows the rate of caryophyllene release during 25 minutes of chewing in terms of the percentage of caryophyllene released from the gum as described in Example 2.
Figure 11:
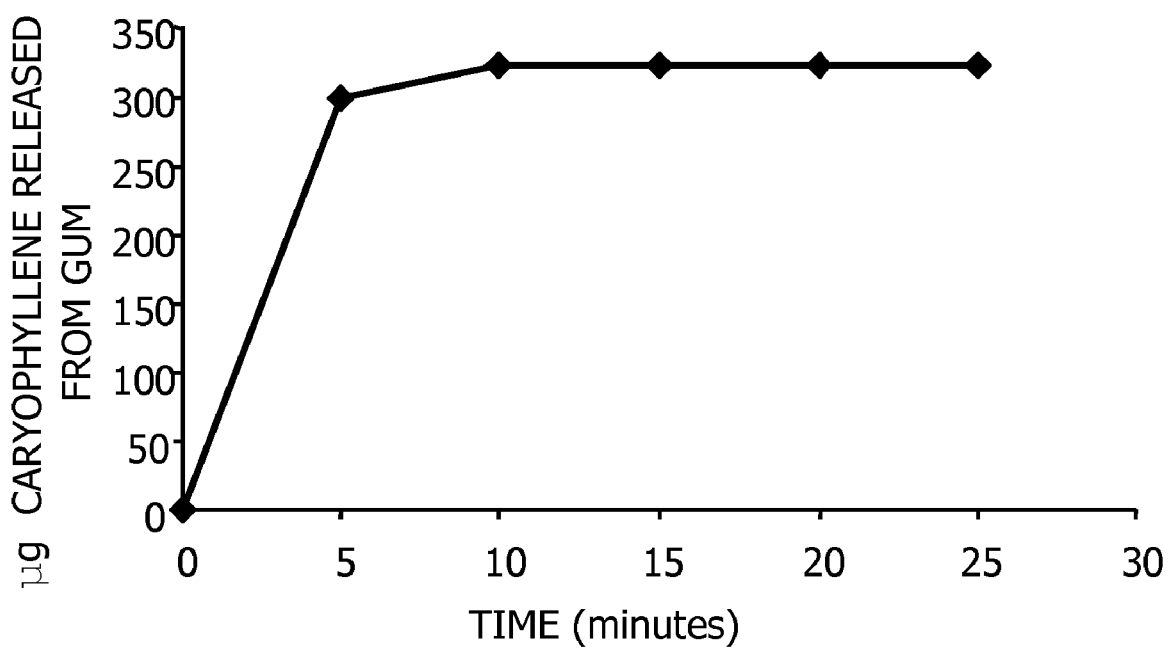
FIG. 11 shows the rate of caryophyllene release during 25 minutes of chewing in terms of the amount of caryophyllene (μg) released from the gum as described in Example 2.

The amount of caryophyllene remaining in the gum after 5, 10, 15, 20 and 25 minutes of chewing was determined. For example, 1.04 mg remained after 25 minutes of chewing. Thus, 23% of the caryophyllene was released during the 25 minutes of chewing. FIGS. 10 and 11 show the rate of caryophyllene release during 25 minutes of chewing in terms of the percentage of caryophyllene released from the gum and amount (μg) of caryophyllene released from the gum, respectively.

Example 3

The following example details testing of menthone for treatment of solutions with characteristic garlic aroma.

Figure 12:
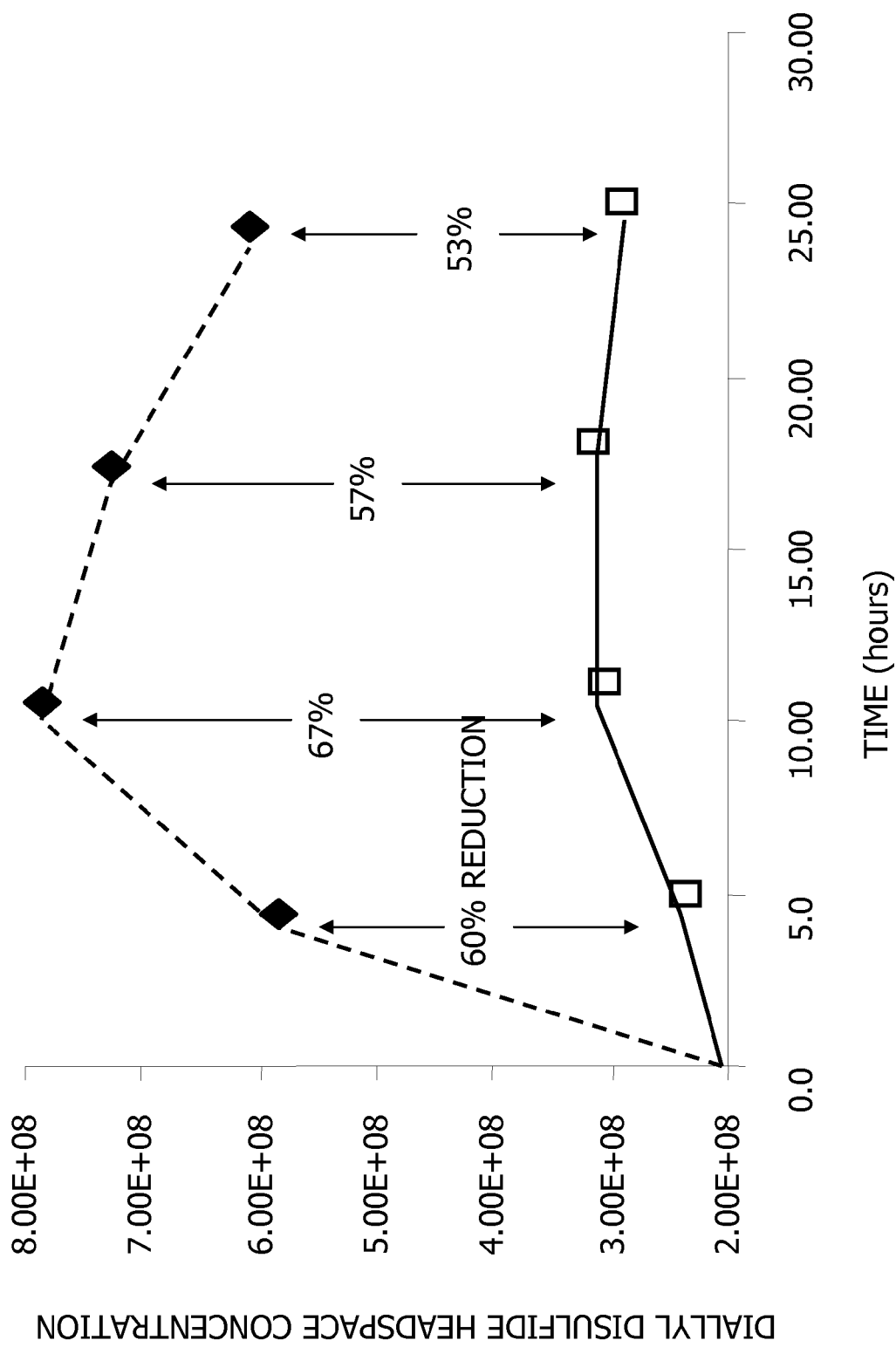
FIG. 12 shows the percent reduction of diallyl disulfide headspace concentration observed with addition of menthone to a raw garlic solution as described in Example 3.

A model solution containing raw chopped garlic dispersed in water was prepared as described in Example 1. Menthone (1.63 mg) was introduced to a portion of the model solution (2.5 g) and a portion of the vessel headspace was extracted and its diallyl disulfide content was analyzed at 5 hour intervals using GC/MS analysis as described in Example 1. For comparison purposes, the diallyl disulfide content of the headspace of a control model solution (i.e., no menthone added) was also analyzed. The results are shown in FIG. 12; as shown, the headspace of the vessel containing the model solution treated with menthone contained at least 50% less diallyl disulfide at each headspace analysis interval.

Example 4

This example details testing of active compositions at varying concentrations for treatment of solutions with characteristic garlic aroma.

Model solutions containing raw chopped garlic dispersed in water were prepared as described in Example 1. Portions of model solution (2.5 g) were treated with menthone, menthone and caryophyllene, or caryophyllene in the following amounts:

| | |
|---|---|
| (1) | 0.5 mg menthone (0.2 mg/g solution) |
| (2) | 1 mg menthone (0.4 mg/g solution) |
| (3) | 1.5 mg menthone (0.6 mg/g solution) |
| (4) | 2 mg menthone (0.8 mg/g solution) |
| (5) | 0.25 mg menthone (0.1 mg/g solution) + 0.25 mg (0.1 mg/g solution) caryophyllene |
| (6) | 0.5 mg menthone (0.2 mg/g solution) + 0.5 mg (0.2 mg/g solution) caryophyllene |
| (7) | 0.75 mg menthone (0.3 mg/g solution) + 0.75 mg (0.3 mg/g solution) caryophyllene |
| (8) | 0.75 mg caryophyllene (0.3 mg/g solution) |
| (9) | 1.5 mg caryophyllene (0.6 mg/g solution) |

A portion of the headspace of the vessel containing each treated solution was extracted and its diallyl disulfide content was analyzed as described in Example 1. For comparison purposes, the diallyl disulfide content of the headspace of vessels containing control model solutions (i.e., no active added) were also analyzed.

Figure 13:
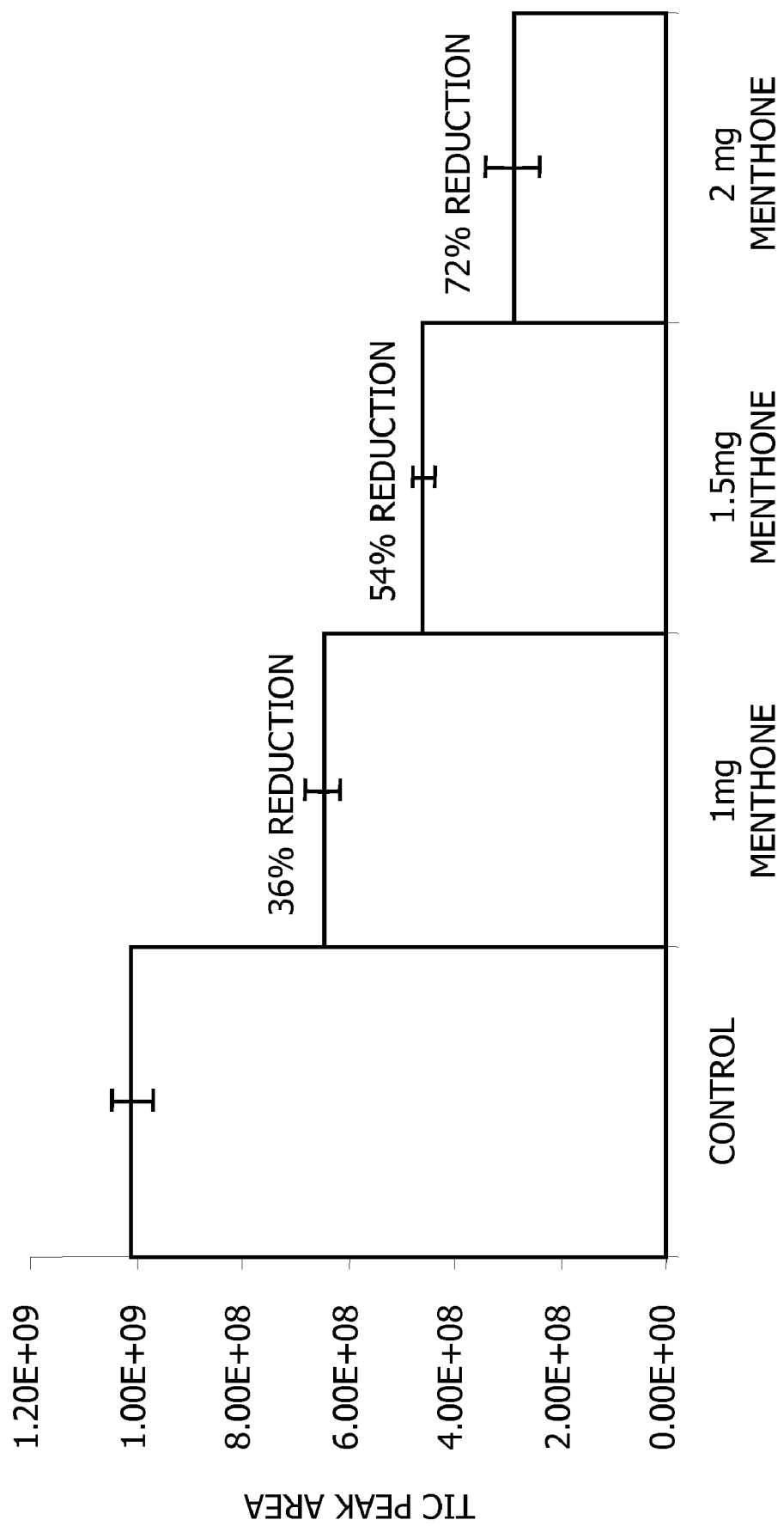
FIG. 13 shows the peak area of total ion current (TIC) chromatograms for various samples as described in Example 4.

FIG. 13 shows the peak area of total ion current (TIC) chromatograms for samples (2)-(4) and a control sample obtained by GC/MS analysis as described in Example 1.

Figure 14:
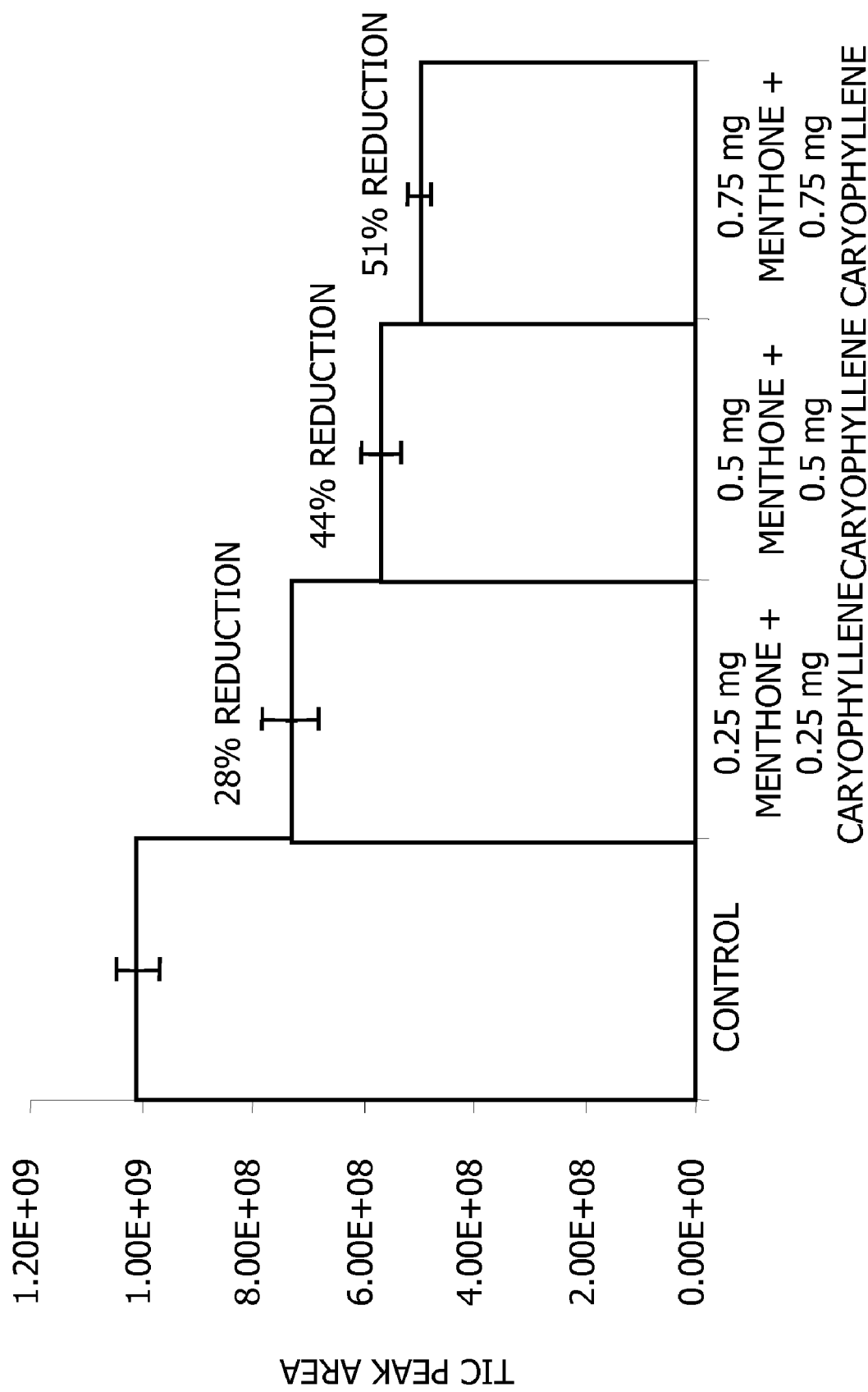
FIG. 14 shows the peak area of total ion current (TIC) chromatograms for various samples as described in Example 4.

FIG. 14 shows the peak area of total ion current (TIC) chromatograms for samples (5)-(7) and a control sample obtained by GC/MS analysis as described in Example 1.

Figure 15:
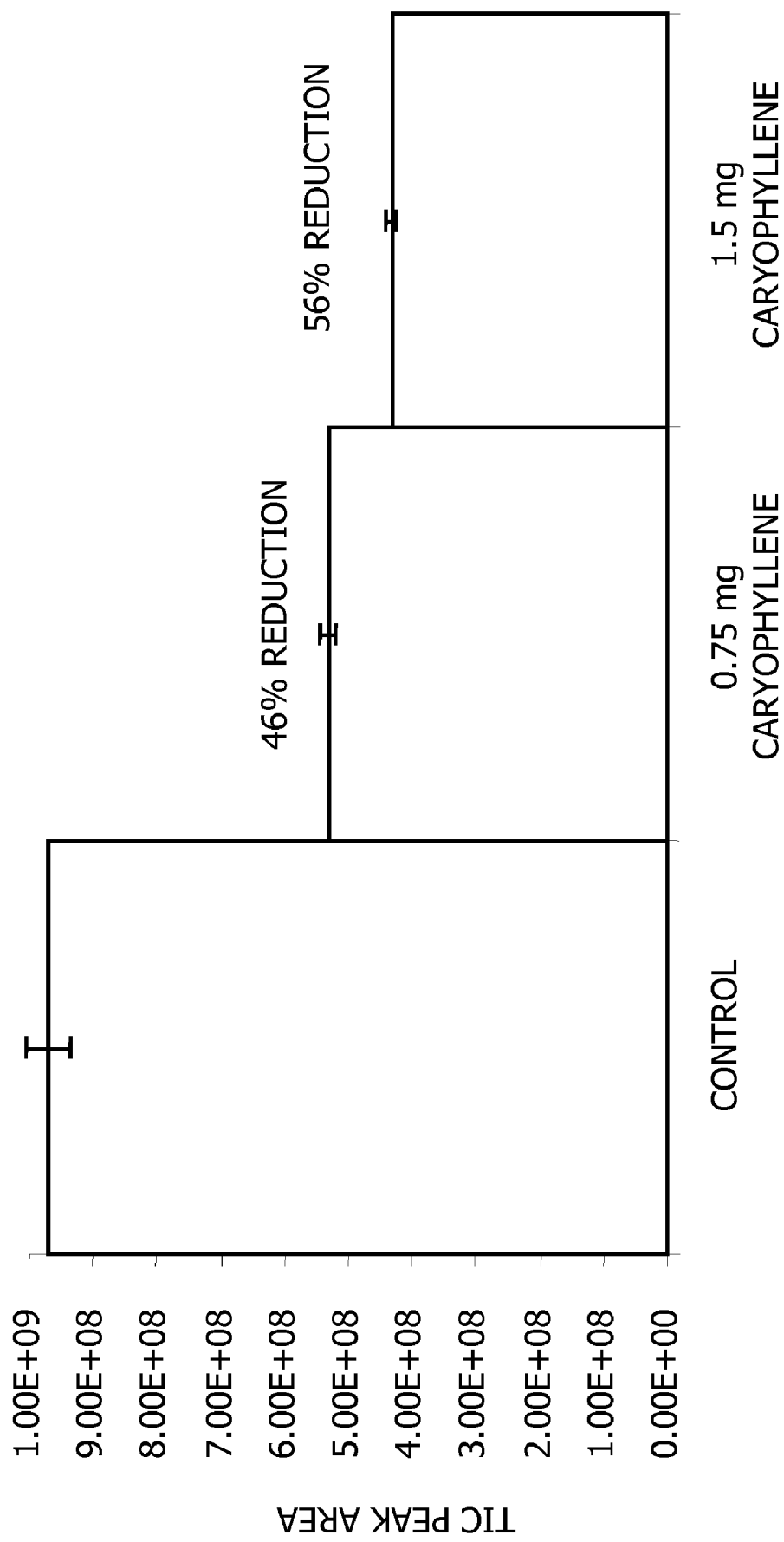
FIG. 15 shows the peak area of total ion current (TIC) chromatograms for various samples as described in Example 4.

FIG. 15 shows the peak area of total ion current chromatograms for samples (8) and (9) and a control sample obtained by GC/MS analysis as described in Example 1.

Figure 16:
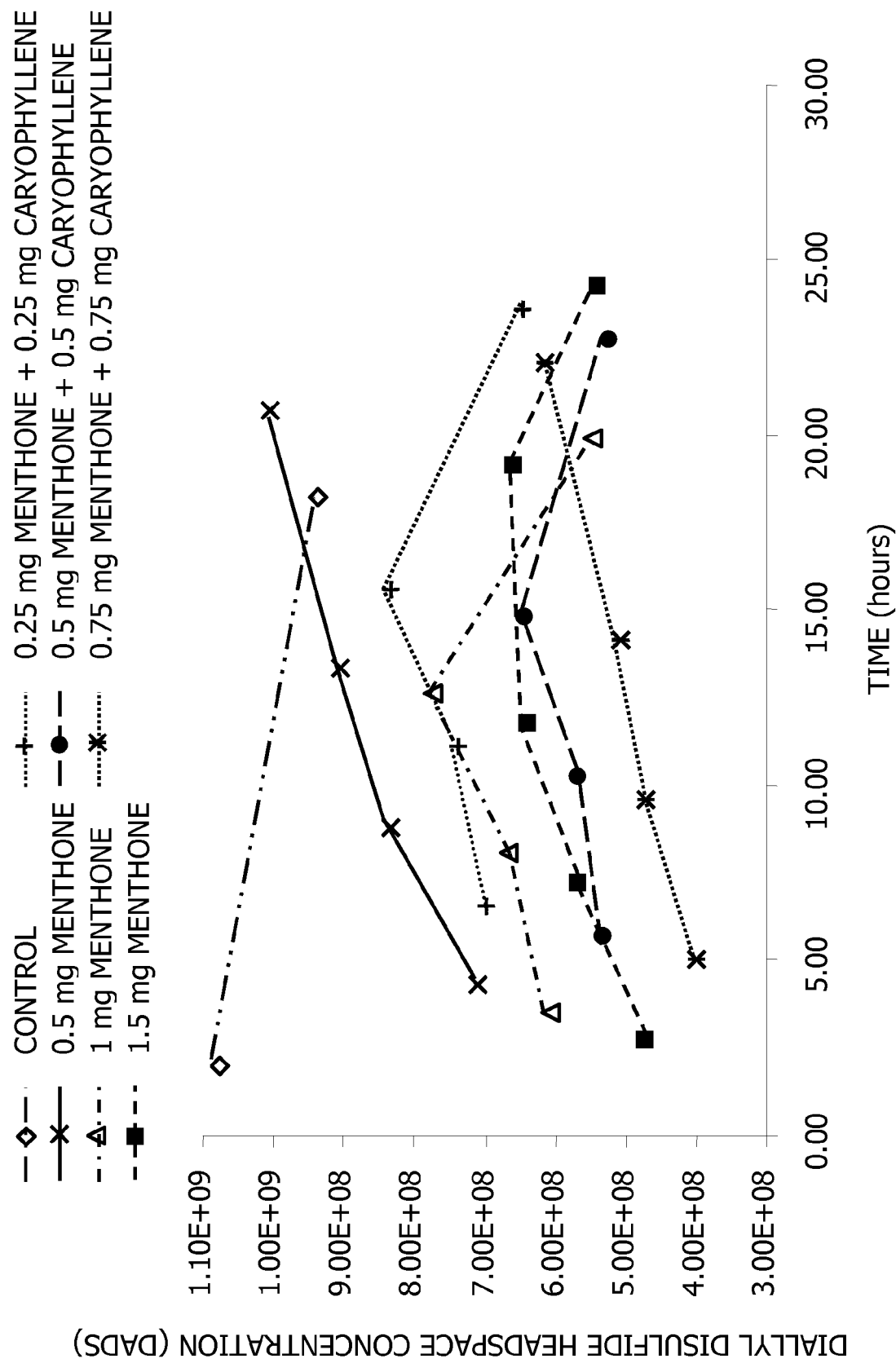
FIG. 16 shows the diallyl disulfide headspace concentration observed with addition of menthone or menthone and caryophyllene to a raw garlic solution as described in Example 4.

FIG. 16 shows the diallyl disulfide concentration determined by GC/MC analysis at 5 hour intervals for a control sample and samples (1)-(3) and (5)-(7).

The present invention is not limited to the above embodiments and can be variously modified. The above description of the preferred embodiments, including the Examples, is intended only to acquaint others skilled in the art with the invention, its principles, and its practical application so that others skilled in the art may adapt and apply the invention in its numerous forms, as may be best suited to the requirements of a particular use.

With reference to the use of the word(s) comprise or comprises or comprising in this entire specification (including the claims below), unless the context requires otherwise, those words are used on the basis and clear understanding that they are to be interpreted inclusively, rather than exclusively, and applicants intend each of those words to be so interpreted in construing this entire specification.

What is claimed is:

1. A method for preparing an oral composition effective for reducing oral malodor associated with consumption of garlic, the method comprising:
   placing a model solution comprising a sulfide or disulfide compound in a vessel;
   measuring a concentration of the sulfide or disulfide compound in a headspace of the vessel, to determine an initial sulfide or disulfide concentration in the headspace;
   contacting a test composition and the model solution in the vessel;
   measuring the concentration of the sulfide or disulfide compound in the headspace of the vessel after contact the model solution and the test composition, to determine a final sulfide or disulfide concentration in the headspace;

identifying a test composition that reduces the concentration of the sulfide or disulfide compound in the headspace of the vessel, the final concentration of the sulfide or disulfide compound being less than the initial concentration thereof; and, preparing an oral composition effective for reducing oral malodor associated with the consumption of garlic comprising said identified test composition.

2. A method as set forth in claim 1 further comprising diluting said test composition prior to said contacting in the vessel.

3. A method as set forth in claim 1 wherein said oral composition comprises a confection, chewing gum, lozenge, pressed tablet, edible film, mouthspray, mouthwash, foam, toothpaste product, or combinations thereof.

4. A method as set forth in claim 1 wherein the test composition is contacted, and optionally agitated, with the model solution in the vessel for at least about 10 minutes at a temperature of about 20° C., prior to measuring the concentration of the sulfide or disulfide compound in the headspace of the vessel containing the test composition and the model solution.

5. A method as set forth in claim 1 wherein measuring the concentration of the sulfide or disulfide compound in the headspace of the vessel, before and/or after contact of the model solution with the test composition, comprises:

sampling a portion of the vapors comprising a sulfide or disulfide compound in the headspace; and subjecting the sampled portion of the vapors to analysis comprising chromatography.

6. A method as set forth in claim 5 wherein said sampling comprises contacting the headspace with a gas tight syringe and extracting a portion of the vapors comprising a sulfide or disulfide compound in the headspace from the vessel, wherein the vessel is hermetically sealed.

7. A method as set forth in claim 5 further comprising subjecting the sampled portion of the vapors to mass spectrometry.

8. A method as set forth in claim 1 wherein said model solution comprises a sulfide or disulfide compound selected from the group consisting of allyl methyl sulfide, dimethyl disulfide, methyl allyl disulfide, methyl-t-propenyl disulfide, diallyl disulfide, and combinations thereof.

9. A method as set forth in claim 8 wherein the concentration of a sulfide compound is reduced by at least about 20%.

10. A method as set forth in claim 8 wherein the concentration of a disulfide compound is reduced by at least about 20%.

11. A method as set forth in claim 1 wherein the test composition comprises menthone, caryophyllene, or a combination thereof.

12. A method as set forth in claim 11 wherein the model solution is contacted with at least about 0.1 mg of the test composition per gram solution.

13. A method as set forth in claim 11 wherein the model solution is contacted with from about 0.1 to about 2 mg of the test composition per gram solution.

14. A method as set forth in claim 1 wherein a plurality of test compositions are each individually contacted with a model solution comprising a sulfide or disulfide compound in a vessel and the ability of each of the test compositions to reduce the concentration of a sulfide or disulfide compound in the headspace of the vessel is determined.

15. A method as set forth in claim 14 wherein a confection or chewing gum is prepared including at least 2 or more of the plurality of test compositions identified for reducing the concentration of the sulfide or disulfide compound in the headspace of the vessel.

16. A method as set forth in claim 15 wherein the at least 2 or more identified test compositions provide the greatest reduction in the concentration of a sulfide or disulfide compound in the headspace of a vessel as compared to all other test compositions of said plurality not included in said confection or chewing gum.

17. A method as set forth in claim 16 wherein the at least 2 or more identified test compositions comprise menthone and caryophyllene.

18. A method as set forth in claim 1 further comprising administering to a subject the oral composition comprising the identified test composition recognized to reduce the concentration of a sulfide or disulfide compound present in said subject's oral cavity as a result of the consumption of garlic.

19. A method for identifying a composition suitable for use in an oral composition effective for reducing oral malodor associated with the consumption of garlic, the method comprising:

placing a model solution comprising allyl methyl sulfide, dimethyl disulfide, methyl allyl disulfide, methyl-t-propenyl disulfide and diallyl disulfide in a vessel;

measuring a concentration of one or more of the allyl methyl sulfide, dimethyl disulfide, methyl allyl disulfide, methyl-t-propenyl disulfide and diallyl disulfide in a headspace of the vessel, to determine an initial concentration thereof in the headspace;

contacting a test composition and the model solution in the vessel;

measuring the concentration of one or more of the allyl methyl sulfide, dimethyl disulfide, methyl allyl disulfide, methyl-t-propenyl disulfide and diallyl disulfide in the headspace of the vessel after contact the test composition and the model solution, to determine a final concentration thereof in the headspace; and, determining the difference between the initial and final concentration of the allyl methyl sulfide, dimethyl disulfide, methyl allyl disulfide, methyl-t-propenyl disulfide or diallyl disulfide in the headspace of the vessel, to identify a test composition that reduces the concentration of one or more of these compounds in said model solution in the headspace of said vessel.

20. A method as set forth in claim 19 wherein said oral composition comprises a confection, chewing gum, lozenge, pressed tablet, edible film, mouthspray, mouthwash, foam, toothpaste product or combinations thereof.

21. A method as set forth in claim 19 wherein the concentration of a sulfide compound is reduced by at least about 20%.

22. A method as set forth in claim 19 wherein the concentration of a disulfide compound is reduced by at least about 20%.

23. A method as set forth in claim 19 wherein the identified test composition comprises menthone, caryophyllene, or a combination thereof.

* * * * *